(12) United States Patent
Rautenstrauch et al.

(10) Patent No.: US 8,809,256 B2
(45) Date of Patent: Aug. 19, 2014

(54) 2-HYDROXY-6-METHYL-HEPTANE DERIVATIVES AS PERFUMING INGREDIENTS

(75) Inventors: Valentin Rautenstrauch, Collonges-sous-Saleve (FR); Piero Fantini, Geneva (CH)

(73) Assignee: Firmenish SA, Geneva (CH)

( * ) Notice: Subject to any disclaimer, the term of this patent is extended or adjusted under 35 U.S.C. 154(b) by 0 days.

(21) Appl. No.: 13/635,571

(22) PCT Filed: Apr. 19, 2011

(86) PCT No.: PCT/IB2011/051690
§ 371 (c)(1),
(2), (4) Date: Sep. 17, 2012

(87) PCT Pub. No.: WO2011/135487
PCT Pub. Date: Nov. 3, 2011

(65) Prior Publication Data
US 2013/0011353 A1    Jan. 10, 2013

Related U.S. Application Data

(60) Provisional application No. 61/329,723, filed on Apr. 30, 2010.

(30) Foreign Application Priority Data

Apr. 30, 2010    (EP) ..................... 10161549

(51) Int. Cl.
| | | |
|---|---|---|
| A61K 8/33 | (2006.01) | |
| A61K 8/34 | (2006.01) | |
| A61Q 13/00 | (2006.01) | |
| A61Q 15/00 | (2006.01) | |
| A61Q 5/02 | (2006.01) | |
| A61Q 5/06 | (2006.01) | |
| C11D 3/50 | (2006.01) | |
| C07C 49/203 | (2006.01) | |
| C07C 49/04 | (2006.01) | |
| C07C 31/125 | (2006.01) | |
| C11B 9/00 | (2006.01) | |
| C07C 33/02 | (2006.01) | |

(52) U.S. Cl.
CPC ............. *C11B 9/0015* (2013.01); *C07C 49/203* (2013.01); *C07C 49/04* (2013.01); *C07C 31/125* (2013.01); *C07C 33/02* (2013.01)
USPC ............. 512/25; 424/76.4; 510/101; 514/772

(58) Field of Classification Search
CPC .................................................... C11B 9/0015
See application file for complete search history.

(56) References Cited

U.S. PATENT DOCUMENTS

| | | | | |
|---|---|---|---|---|
| 3,592,856 A | * | 7/1971 | Offenhauer et al. | 568/390 |
| 3,704,714 A | | 12/1972 | Kallianos et al. | 131/17 R |
| 5,840,992 A | * | 11/1998 | Kido et al. | 568/392 |
| 6,238,898 B1 | | 5/2001 | Hausler et al. | 435/155 |
| 2005/0004401 A1 | * | 1/2005 | Barnicki et al. | 568/390 |
| 2007/0105749 A1 | * | 5/2007 | Gaudin | 512/25 |

FOREIGN PATENT DOCUMENTS

| | | | |
|---|---|---|---|
| JP | 56-135431 A | | 10/1981 |
| JP | 57-128612 A | | 8/1982 |
| JP | 60-146811 A | | 8/1985 |
| JP | 2282339 A | * | 11/1990 |

OTHER PUBLICATIONS

Machine Translation of JP 2282339 A abstract.*
International Search Report and Written Opinion of the International Searching Authority, application No. PCT/IB2011/051690, mailed Aug. 4, 2011.

* cited by examiner

*Primary Examiner* — Kevin S Orwig
*Assistant Examiner* — Dominic Lazaro
(74) *Attorney, Agent, or Firm* — Winston & Strawn LLP

(57) ABSTRACT

The invention relates to a method of use of certain derivatives of formula (I)

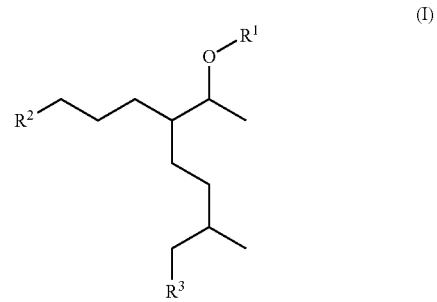

(I)

in the form of any one of its stereoisomers or a mixture thereof, and wherein $R^1$ represents a hydrogen atom, a $C_{1-4}$ alkyl or alkenyl group, or a $(CHR)_2OH$ group, each R being a hydrogen atom or a methyl group; $R^2$ represents a hydrogen atom or a methyl, ethyl or n-propyl group; and $R^3$ represents a hydrogen atom or a methyl group, as perfuming ingredients. The present invention concerns also certain compounds and compositions or articles containing such compounds.

15 Claims, No Drawings

2-HYDROXY-6-METHYL-HEPTANE DERIVATIVES AS PERFUMING INGREDIENTS

This application is a 371 filing of International Patent Application PCT/IB2011/051690, filed on Apr. 19, 2011, and claims the benefit of U.S. provisional application No. 61/329,723 filed on Apr. 30, 2010.

TECHNICAL FIELD

The present invention relates to the field of perfumery. More particularly, it concerns some derivatives of 2-hydroxy-3-alkyl-6-alkyl-heptane of formula (I) herein below, and their use as perfuming ingredients. Moreover, the present invention comprises also the embodiments wherein the invention's compound is part of a perfuming composition or of a perfuming consumer product.

PRIOR ART

To the best of our knowledge none of the invention's compounds is known in the prior art.

Some analogues are known in the literature. In particular, U.S. Pat. No. 3,549,714, discloses some derivatives of 3-hydroxy-7-methyl-octane and their use in perfumery. The closest analogue disclosed in said document is 3-hydroxy-4-ethyl-7-methyl-octane, which possesses a floral fruity odor totally different from the one of the present invention's compounds. Another analogue disclosed in the prior art is a derivative of 2-hydroxy-3-isopropyl-6-methyl-heptane, described in U.S. Pat. No. 3,704,714, as tobacco flavor to reinforce the robustness and the sweetness of the tobacco flavor. The last known analogue is 2-hydroxy-3-isopentyl-6-methyl-heptane, described in JP 60146811 (CA 104:10396), as chemical intermediate for the preparation of cosmetic additives.

However, this prior art document does not report or suggest any organoleptic properties of the compounds of formula (I), or any use of said compounds in the field of perfumery.

DESCRIPTION OF THE INVENTION

We have now surprisingly discovered that a compound of formula

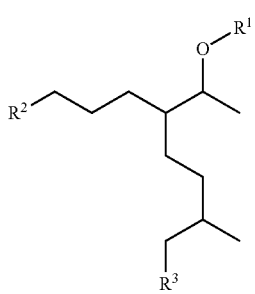

(I)

in the form of any one of its stereoisomers or a mixture thereof, and wherein $R^1$ represents a hydrogen atom, a $C_{1-4}$ alkyl or alkenyl group, or a $(CHR)_2OH$ group, each R being a hydrogen atom or a methyl group;
$R^2$ represents a hydrogen atom or a methyl, ethyl or n-propyl group; and
$R^3$ represents a hydrogen atom or a methyl group;

can be used as perfuming ingredient, for instance to impart odor notes of the green and aromatic and/or earthy-rooty type.

According to a particular embodiment of the invention, said $R^1$ represents a hydrogen atom, a methyl or ethyl group, or a $(CHR)_2OH$ group, one R being a hydrogen atom or a methyl group and the other a hydrogen atom. Alternatively said $R^1$ represents a hydrogen atom or a $(CHR)_2OH$ group.

According to any one of the above embodiments of the invention, said $R^2$ represents a hydrogen atom or a methyl group.

According to any one of the above embodiments of the invention, said $R^3$ represents a hydrogen atom.

According to any one of the above embodiments of the invention, the compound (I) or (II) is a $C_{11}$-$C_{14}$ compound, or even a $C_{11}$ or $C_{12}$ compound.

As specific examples of the invention's compounds, one may cite, as non-limiting example, 6-methyl-3-propylheptan-2-ol which possesses a very nice and natural green-aromatic and pyrazinic note with an aromatic, earthy and rooty connotation. The overall odor may evoke the gentian or the green note of a narcissus. This odor is quite surprising for an aliphatic alcohol which in general possesses a fatty, solvent and hay-like connotation instead of a natural green note.

As other specific, but non-limiting, examples of the invention's compounds, one may cite the following ones in Table 1:

TABLE 1

Invention's compounds and their odor properties

| Compound structure and name | Odor notes |
|---|---|
| Mixture of 5,9-dimethyl-6-propyl-4-oxadecan-2-ol and 2,4,8-trimethyl-5-propyl-3-oxanonan-1-ol | Green, leafy, pyrazinique and minty note |
| 3-butyl-6-methylheptan-2-ol | A green-narcissus and aromatic gentian note close to the odor of its analogue 6-methyl-3-propylheptan-2-ol |

According to a particular embodiment of the invention, the compound of formula (I) is 6-methyl-3-propylheptan-2-ol or 3-butyl-6-methylheptan-2-ol.

When the odor of the invention's compounds is compared with that of the prior art analogues mentioned above in U.S. Pat. No. 3,704,714, then the invention's compounds distinguish themselves by possessing an aromatic connotation as well as a green, pyrazinic note which are absent from the prior art analogues. The odor of the invention's compounds is also lacking, or not possessing significant, sweet floral or fruity notes. Said differences lend the invention's compounds and the prior art compounds to be each suitable for different uses, i.e. to impart different organoleptic impressions.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of formula (I). Moreover, by "perfuming co-ingredient" it is meant here a compound which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:
i) as perfuming ingredient, at least one compound of formula (I), as defined above; and
ii) a fine or functional perfumery base;
is also an object of the present invention.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "fine or functional perfumery base" we mean here a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the fine or functional perfumery base do not warrant a more detailed description here, which in any case would not be exhaustive, the skilled person being able to select them on the basis of his general knowledge and according to the nature and the desired effect of said product.

Non-limiting examples of suitable fine or functional perfumery base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oils or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 25% by weight, or even more, of the compounds of the invention based on the weight of the composition into which they are incorporated. Concentrations lower than these, such as in the order of 0.001% to 15% by weight, can be used when these compounds are incorporated into perfumed articles, percentage being relative to the weight of the article.

The invention's compounds can be prepared according to various methods, which include as key step a Claisen rearrangement or an alkylation, followed by one or more reduction steps. These methods are described in the herein below Schemes:

Scheme 1: Examples of reaction scheme to obtain the invention product via a ketone

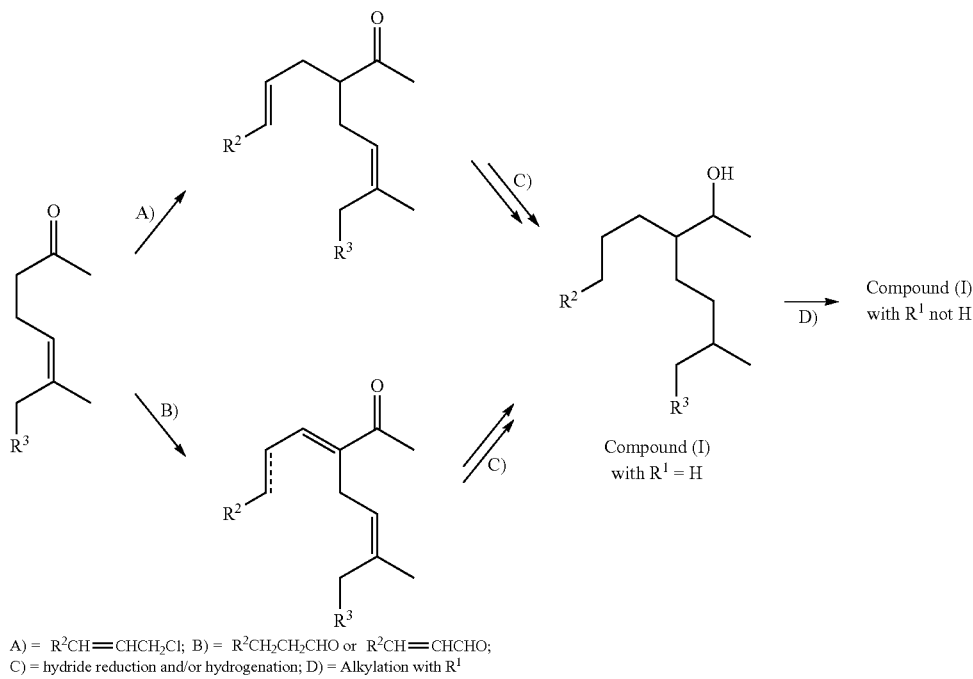

A) = $R^2CH=CHCH_2Cl$; B) = $R^2CH_2CH_2CHO$ or $R^2CH=CHCHO$;
C) = hydride reduction and/or hydrogenation; D) = Alkylation with $R^1$ Scheme 2: Example of reaction scheme to obtain the invention product via a Claisen rearrangement

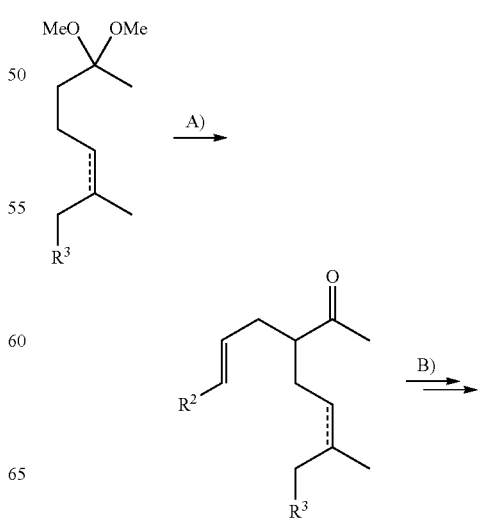

-continued

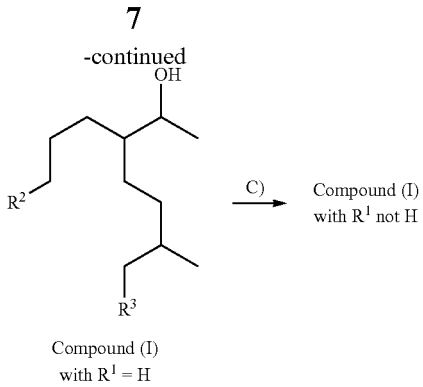

Compound (I) with $R^1$ not H

Compound (I) with $R^1$ = H

A) = $R^2CH=CHCH_2OH$;
B) = hydride reduction and/or hydrogenation; C) = Alkylation with $R^1$ The intermediates to obtain the compounds of formula (I) are novel and useful compounds, with the exception of 3-allyl-6-methylhept-5-en-2-ol (reported in JP 57128612 in the context of terpenic alcohols as controlling agents against underwater injurious organism). The compound of formula (I) are also novel compounds. Therefore another object of the present invention is a compound of formula

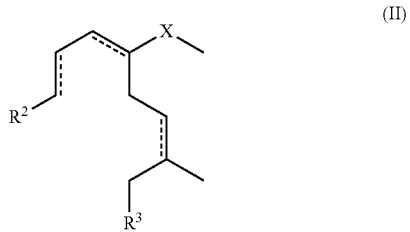

(II)

wherein $R^2$ and $R^3$ are as defined above in any one of the embodiments of formula (I);
X represents a group C=O or $CHOR^1$, $R^1$ being defined as above in any one of the embodiments of formula (I); and each dotted line, independently from each other, represents a carbon-carbon single or double bond, provided that 3-allyl-6-methylhept-5-en-2-ol is excluded.

For the sake of clarity, by the expression "dotted line represents a carbon-carbon single or double bond", or the similar, it is meant the normal meaning understood by a person skilled in the art, i.e. that the whole bonding (solid and dotted line) between the carbon atoms connected by said dotted line is a carbon-carbon single or double bond.

According to a particular embodiment of formula (II), one dotted line represents a carbon-carbon single bond and the other two represent a carbon-carbon single or double bond. Moreover, two dotted lines represent a carbon-carbon single bond and the other, in particular the one which is bound to the $R^2$ group, represents a carbon-carbon single or double bond. Moreover, all dotted lines represent carbon-carbon single bonds.

Alternatively, said compound of formula (II) is a compound of formula (I).

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

a) Preparation of 6-methyl-3-propylheptan-2-ol

Route I)

3-allyl-6-methylhept-5-en-2-one

Methyl heptenone (126.8 g, 1.01 mol), toluene (120.5 g) and 45% aqueous KOH (345.1 g, 2.77 mol) were charged into a 1 liter, 4-necked round bottom flask. The biphasic mixture was heated to 70° C. under stirring.

To this mixture was added, over 2 h30 min at 70° C., a solution of allyl chloride (99.2 g, 1.28 mol) and Aliquat 336 (6.39 g, 0.015 mol) in toluene (12.0 g). After 17 hours, a new solution of allyl chloride (50.5 g, 0.654 mol) and Aliquat 336 (6.96 g, 0.016 mol) in toluene (12.0 g) was added over 30 minutes at 70° C. After 1 hour at 70° C., the reaction mixture was cooled to room temperature, and water (250 ml) was added. The lower aqueous phase was discarded and the organic phase was washed with 12.5% aqueous $H_3PO_4$ (200 ml), water (150 ml), 25% aqueous $KHCO_3$ (110 ml) and 25% aqueous NaCl (150 ml). Drying over $Na_2SO_4$ and evaporation of the solvent afforded a crude product. Fractional distillation of the crude product though a Fischer column afforded the desired compound (68.07 g; 41% yield).

$^1$H-NMR: 1.60 (br s, 3H); 1.68 (br s, 3H); 2.11 (s, 3H); 2.13-2.38 (m, 4H); 2.58 (quintet, J=7 Hz, 1H); 4.98-5.06 (m, 3H); 5.66-5.77 (m, 1H).
$^{13}$C-NMR: 17.8 (q), 25.8 (q), 26.9 (q), 29.8 (t), 35.3 (t), 52.8 (d), 116.7 (t), 121.0 (d), 133.8 (s), 135.7 (d), 211.7 (s).

6-methyl-3-propylheptan-2-ol

The starting 3-allyl-6-methylhept-5-en-2-one (69.80 g, 420 mmol) was dissolved in methanol (80 ml) and hydrogenated in the presence of Raney Nickel (Actimet; 5.3 g). The hydrogen pressure was progressively increased to 200 bar, and the reaction ran for 120 hours to achieve complete conversion. The catalyst was filtered off and the solvent removed under vacuum. The crude product was purified by fractional distillation, affording 64.5 g of pure alcohol (89% yield).

$^1$H NMR: 3.82 (m, 1H); 1.50 (br s, 1H, OH); 1.55-1.12 (m, 10H); 1.37 (d, J=6.7 Hz, 3H); 0.90 (m, 3H); 0.88 (d, J=6.4 Hz, 6H).
$^{13}$C NMR: 14.6 (q), 19.8 (q), 20.7 (t), 22.6 (q), 22.7 (q), 27.3 (t), 28.5 (d), 32.0 (t), 36.8 (t), 45.0 (d), 69.6 (d).

Route II)

(E)-6-methyl-3-propylideneheptan-2-one

Anhydrous $MgCl_2$ (27.0 g, 284 mmol) was charged into a 1 liter, 4-necked round bottom flask, and ethyl acetate (150 ml) was added. The suspension was stirred at room temperature, and a solution of $TiCl_3(OiPr)$ (34% in ethyl acetate; 21.50 g, 34.3 mmol) was added dropwise over 1.5 hour. The reaction mixture was stirred overnight at room temperature, and after that heated to 70° C. 6-Methyl 2-heptanone (110.0 g, 858 mmol) was added over 2.5 hours, followed by a slow addition of propanal (105.0 g, 1716 mmol) over 6 hours.

Stirring at 70° C. was continued for 22 hours. After cooling at room temperature, the black reaction mixture was poured onto a mixture of ice (100 g), water (300 ml) and 25% aqueous $H_3PO_4$ (100 ml). The aqueous phase was discarded and the organic phase washed with 25% aq. potassium citrate, then twice with 10% aqueous $K_2CO_3$ and twice with brine. Drying over $Na_2SO_4$ and evaporation of the solvent afforded the crude product. Fractional distillation though a Vigreux column followed by a second distillation through a Fischer column afforded the desired ketone (32.0 g, 22.2% yield).

$^1$H-NMR: 0.90 (d, J=6.6, 6H); 1.09 (t, J=7.1, 3H); 1.13-1.19 (m, 2H); 1.54 (m, 1H);

2.22-2.28 (m, 4H); 2.29 (s, 3H); 5.55 (t, J=7.3, 1H).

$^{13}$C-NMR: 13.5 (q), 22.2 (t), 22.5 (2q), 23.4 (t), 25.6 (q), 28.4 (d), 38.6 (t), 142.2 (s), 145.0 (d), 199.6 (s).

6-methyl-3-propylheptan-2-ol

The product was obtained in similar yield by hydrogenating (E)-6-methyl-3-propylideneheptan-2-one using the same protocol as described in Route I).

Route III)

3-allyl-6-methylhept-5-en-2-one

Methyl heptenone (126.8 g, 1.01 mol) toluene (120.5 g) and 45% aqueous KOH (345.1 g, 2.77 mol) were charged into a 1 liter, 4-necked round bottom flask. The biphasic mixture was heated to 70° C. under stirring.

A solution of allyl chloride (99.2 g, 1.28 mol) and Aliquat® 336 (6.39 g, 0.015 mol) in toluene (12.0 g) was added over 2 h30 min at 70° C. After 17 h a new solution of allyl chloride (50.5 g, 0.654 mol) and Aliquat® 336 (6.96 g, 0.016 mol) in toluene (12.0 g) was added over 30 min at 70° C. After 1 h at 70° C., the reaction mixture was cooled to room temperature, and water (250 ml) was added. The lower aqueous phase was discarded and the organic phase was washed with 12.5% aqueous $H_3PO_4$ (200 ml), water (150 ml), 25% aqueous $KHCO_3$ (110 ml) and 25% aqueous NaCl (150 ml). Drying over $Na_2SO_4$ and evaporation of the solvent afforded the crude product. Fractional distillation though a Fischer column afforded the desired compound (68.07 g, 41% yield).

$^1$H-NMR: 1.60 (br s, 3H); 1.68 (br s, 3H); 2.11 (s, 3H); 2.13-2.38 (m, 4H); 2.58 (quintet, J=7, 1H); 4.98-5.06 (m, 3H); 5.66-5.77 (m, 1H).

$^{13}$C-NMR: 17.8 (q), 25.8 (q), 26.9 (q), 29.8 (t), 35.3 (t), 52.8 (d), 116.7 (t), 121.0 (d), 133.8 (s), 135.7 (d), 211.7 (s).

3-allyl-6-methylhept-5-en-2-ol 3-allyl-6-methylheptenone (20.0 g, 120 mmol) was dissolved in anhydrous THF (100 ml) and the solution cooled to −15° C. under stirring. A 3.5M solution of $LiAlH_4$ (in THF/toluene, 12.0 ml, 42 mmol, 0.35 mol. eq.) was added dropwise under argon over 30 min. The reaction mixture was then stirred at −15° C. for 1 hour. The temperature was raised to 0° C., and the mixture carefully hydrolyzed by successive dropwise additions of water (1.60 g), 15% aqueous NaOH (1.60 g) and water (4.80 g), while keeping the reaction mixture at 0° C. The mixture was allowed to warm to room temperature, and the precipitate filtered. Evaporation of the solvent afforded the crude product. Fractional distillation though a 10 cm Vigreux column afforded the desired compound (16.94 g (83% yield).

$^1$H-NMR: 1.17 (d, J=6.3, 3H); 1.49-1.56 (m, 1H); 1.62 (br s, 3H); 1.65 (br s, 1H, OH); 1.70 (br s, 3H); 1.937-2.241 (m, 4H); 3.83 (m, 1H); 4.99-5.04 (m, 2H); 5.07 (m, 1H); 5.12-5.18 (m, 1H).

$^{13}$C-NMR: 17.9 (q), 20.0 (q), 25.9 (q), 28.2 (t), 34.5 (t), 45.5 (d), 69.6 (d), 116.1 (t), 123.0 (d), 132.7 (s), 137.7 (d).

6-methyl-3-propylheptan-2-ol

The product was obtained in similar yield by hydrogenating (E)-6-methyl-3-propylideneheptan-2-one using the same protocol as described in Route I).

b) Preparation of 3-butyl-6-methylheptan-2-ol

E/Z 3-(but-en-1-yl)-6-methylhept-5-en-2-one

In a 1 liter 4-necked flask, equipped with a mechanical stirrer, 6-methylhept-5-en-2-one (126.81 g, 1.00 mol) was dissolved in toluene (125 ml). An aqueous solution of KOH (45%, 354.15 g, 2.84 mol) was added at room temperature. The biphasic mixture was heated to 70° C. under stirring. A solution of PTC catalyst (trioctyl methyl ammonium chloride, Aliquat 336, 6.46 g, 16 mmol), and crotyl chloride (136.4 g, 1.51 mol) in toluene (10.0 g) was then added over 2.5 hours at 70° C. The mixture was then cooled to room temperature and stirred overnight. A partial conversion into the desired compound was observed. The crude reaction mixture was poured onto water (250 ml), and washed successively with aqueous $H_3PO_4$ (12.5%, 400 ml), aqueous NaCl (15%, 250 ml), $NaHCO_3$ (5%, 100 ml) and 3 times with aqueous NaCl (25%, 100 ml). After drying over $Na_2SO_4$ and filtration, the solvent was removed in vacuuo. The concentrated product was distilled through a Vigreux column A second distillation through a Fischer column afforded the desired product (as a 4/1 mixture of E and Z isomers).

$^1$H NMR: 5.56-5.39 (m, 1H); 5.37-5.26 (m, 1H); 5.02 (m, 1H); 2.56-2.48 (m, 1H); 2.35-2.08 (m, 4H); 2.09 (s, 3H); 1.68 (brs, 3H); 1.63 (dd, J=6.3, 1, 3H), 1.59 (brs, 3H).

$^{13}$C NMR: 17.8 (q); 17.9 (q); 25.8 (q); 29.5 (q); 29.7 (t); 34.2 (t); 53.3 (d); 121.2 (d); 127.4 (d); 128.0 (d); 133.6 (s); 212.1 (s).

6-methylheptan-3-butyl-2-one 3-(but-2-en-1-yl)-6-methylhept-5-en-2-one (10.0 g, 55.5 mmol) was dissolved in cyclohexane (100.0 ml). The catalyst (Pd/C 5%, 0.387 g) was added and the mixture was hydrogenated under 1 atm $H_2$ at room temperature under stirring. After 20 h, the catalyst was filtered, and the solvent removed under vacuum. The crude ketone was distilled bulb-to-bulb (Kugelrohr), (oven 50° C., 0.2 mbar) affording the desired product: 8.50 g (83.2% yield).

$^1$H-NMR: 2.34-2.43 (m, 1H); 2.11 (s, 3H); 1.36-1.63 (m, 5H); 1.06-1.35 (m, 6H); 0.88 (t, J=7.1, 3H); 0.87 (d, J=6.5, 6H).

$^{13}$C NMR: 13.9 (q); 22.4 (q); 22.5 (q); 22.8 (t); 28.2 (d); 28.6 (q); 29.6 (t); 29.7 (t); 31.5 (t); 36.6 (t); 53.5 (d); 213.1 (s).

3-butyl-6-methylheptan-2-ol 3-butyl-6-methylheptan-2-one (5.00 g, 27.1 mmol) was dissolved in dry THF (70 ml). The solution was cooled to −15° C., and a suspension of $LiAlH_4$ (3.5M, 2.7 ml, 9.45 mmol) was added over 15 minutes under stirring. After one hour at −15° C., a complete conversion was observed. The grey suspension was warmed to 0° C., and hydrolyzed by slow and successive addition of: water (0.36 g), 15% aqueous NaOH (0.36 g) and water (1.08 g). After warming to room temperature, the white precipitate was filtered, and the solvent removed under vacuum. The crude product was distilled bulb-to-bulb (Kugelrohr, oven 50° C., 0.2 mbar) (yield: 74.5%).

$^1$H NMR: 3.82 (m, 1H); 1.57-1.16 (m, 13H); 1.14 (d, J=6.4, 3H); 0.90 (t, J=6.9, 3H); 0.88 (d, J=6.7, 6H).

$^{13}$C NMR: 14.1 (q); 19.9 (q); 22.6 (q); 22.6 (q); 23.2 (t); 27.3 (t); 28.5 (d); 29.3 (t); 29.8 (t); 36.8 (t); 45.2 (d); 69.6 (d).

Example 2

Preparation of a Perfuming Composition

A perfuming composition for a functional application was prepared by admixing the following ingredients:

| Ingredient | Parts by weight |
|---|---|
| Benzyl acetate | 750 |
| Cis-3-hexenol acetate | 50 |
| Styrallyl acetate | 50 |
| Hexylcinnamic aldehyde | 350 |
| 10%* Aldolone ®[1)] | 50 |
| *Artemisia* essential oil | 50 |
| Methyl benzoate | 25 |
| Camphor | 50 |
| Allyl caproate | 25 |
| Carvone Gauche | 25 |
| Citronellyl nitrile | 25 |
| Cyclamen aldehyde | 25 |
| Dihydroestragol | 50 |
| Dihydromyrcenol | 500 |
| *Eucalyptus* essential oil | 50 |
| Eugenol | 50 |
| Diethyl 1,4-cyclohexane dicarboxylate[2)] | 100 |
| Geraniol | 150 |
| Habanolide ®[3)] | 250 |
| Hedione ®[4)] | 250 |
| Phenox isobutyrate | 300 |
| Lilial ®[5)] | 200 |
| 10%* Methylparacresol | 100 |
| Muscenone[6)] Delta | 25 |
| Phenethylol | 300 |
| Terpineol | 100 |
| 10%** Violettyne[7)] | 50 |
| 2,4-Dimethyl-3-cyclohexene-1-carbaldehyde | 50 |
| | 4000 |

*in dipropyleneglycol
**in isopropyl myristate
[1)] 7-propyl-2H,4H-1,5-benzodioxepin-3-one; origin: Firmenich SA, Geneva, Switzerland
[2)] origin: Firmenich SA, Geneva, Switzerland
[3)] pentadecenolide; origin: Firmenich SA, Geneva, Switzerland
[4)] methyl cis-dihydrojasmonate; origin: Firmenich SA, Geneva, Switzerland
[5)] 3-(4-tert-butylphenyl)-2-methylpropanal; origin: Givaudan SA, Vernier, Switzerland
[6)] 3-methyl-5-cyclopentadecen-1-one; origin: Firmenich SA, Geneva, Switzerland
[7)] 1,3-undecadien-5-yne; origin: Firmenich SA, Geneva, Switzerland The addition of 1000 parts by weight of 6-methyl-3-propylheptan-2-ol to the above-described composition imparted to the latter a natural green, gentian (earthy, rooty) note, and pouched also the artemisia green-aromatic note. The fragrance thus obtained acquired a very natural, diffusing and sparkling green acid effect.

The use of the prior art 3-hydroxy-4-ethyl-7-methyl-octane imparted a typical sweet floral fruity note which unbalanced the overall fragrance.

Example 3

Preparation of a Perfuming Composition

An eau de cologne, of the herbaceous and green type, was prepared by admixing the following ingredients:

| Ingredient | Parts by weight |
|---|---|
| Geranyl acetate | 10 |
| Linalyl acetate | 200 |
| Allyl amyl glycolate | 80 |
| 10%* Ambrox ®[1)] Super | 60 |
| 10%* Methyl anthranilate | 20 |
| Bergamote essential oil | 480 |
| Citral | 20 |
| Citronellol | 20 |
| 10%* Damascone Alpha | 80 |
| 50%* Mousse Chêne | 60 |
| 10%* Galbanum essential oil | 60 |
| Galbex ®[2)] | 150 |
| Juniper essential oil | 60 |
| Geraniol | 20 |
| *Geranium* essential oil | 40 |
| Hedione ®[3)] | 300 |
| 10%* 3-(1,3-benzodioxol-5-yl)-2-methylpropanal | 50 |
| Hydroxycitronellal | 50 |
| Iralia ®[4)] Total | 100 |
| Iso E ®[5)] Super | 150 |
| 1%* Labdanum essential oil | 50 |
| Lavandin Grosso | 150 |
| Linalool | 100 |
| Lyral ®[6)] | 80 |
| Mint essential oil | 10 |
| 1%* Methyl 2-Octynoate | 40 |
| Methyl naphthyl ketone | 20 |
| Crystal moss | 20 |
| Nutmeg essential oil | 40 |
| 10%* Rose oxide | 20 |
| Orange essential oil | 100 |
| 1-Methyl-4-(4-methyl-3-pentenyl)-3-cyclohexene-1-carbaldehyde | 60 |
| Amyl salicylate | 30 |
| 3-Methyl-5-(2,2,3-trimethyl-3-cyclopenten-1-yl)-2-pentanol | 20 |
| Clary sage essential oil | 40 |
| Tonalide ®[7)] | 300 |
| Vertofix ®[8)] Coeur | 400 |
| 2,4-Dimethyl-3-cyclohexene-1-carbaldehyde | 10 |
| | 3500 |

*in dipropyleneglycol
**in isopropyl myristate
[1)] (−)-(8R)-8,12-epoxy-13,14,15,16-tetranorlabdane; origin: Firmenich SA, Geneva, Switzerland
[2)] specialty base; origin: Firmenich SA, Geneva, Switzerland
[3)] methyl cis-dihydrojasmonate; origin: Firmenich SA, Geneva, Switzerland
[4)] mixture of methylionones isomers; origin: Firmenich SA, Geneva, Switzerland
[5)] 1-(octahydro-2,3,8,8-tetramethyl-2-naphthalenyl)-1-ethanone; origin: International Flavors & Fragrances, USA
[6)] 4/3-(4-hydroxy-4-methylpentyl)-3-cyclohexene-1-carbaldehyde; origin: International Flavors & Fragrances, USA
[7)] (5,6,7,8-tetrahydro-3,5,5,6,8,8-hexamethyl-2-naphthyl)-1-ethanone; origin: Givaudan SA, Vernier, Switzerland
[8)] methyl cedryl ketone; origin: International Flavors & Fragrances, USA The addition of 500 parts by weight of 6-methyl-3-propylheptan-2-ol to the above-described composition reinforced the latter's green note, adding also a narcissus (earthy, rooty) note.

What is claimed is:
1. A method to confer, enhance, improve or modify odor properties of a perfuming composition or of a perfumed article, which method comprises adding to said composition or article an effective amount of at least a compound of 6-methyl-3-propylheptan-2-ol or 3-butyl-6-methylheptan-2-ol in the form of any one of its stereoisomers or a mixture thereof to impart earthy/green odor characters thereto.

2. The method according to claim 1, wherein the compound is added to a perfuming composition comprising:
   i) at least one ingredient selected from the group consisting of a perfumery carrier and a perfumery base; and
   optionally at least one perfumery adjuvant.

3. The method according to claim 1, wherein the compound is added to a perfuming consumer product or article that includes:
   a fine or functional perfumery base.

4. The method according to claim 3, wherein the fine or functional perfumery base is a perfume, a fabric care product, a body-care product, an air care product or a home care product.

5. The method according to claim 3, wherein the fine or functional perfumery base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oils or gel, a hygiene product, an air freshener, a "ready to use" powdered air freshener, a wipe, a dish detergent or hard-surface detergent.

6. The method according to claim 1 wherein the compound is 6-methyl-3-propylheptan-2-ol in the form of any one of its stereoisomers.

7. The method according to claim 1 wherein the compound is 3-butyl-6-methylheptan-2-ol in the form of any one of its stereoisomers.

8. The method according to claim 2 wherein the compound is 6-methyl-3-propylheptan-2-ol in the form of any one of its stereoisomers.

9. The method according to claim 2 wherein the compound is 3-butyl-6-methylheptan-2-ol in the form of any one of its stereoisomers.

10. The method according to claim 3 wherein the compound is 6-methyl-3-propylheptan-2-ol in the form of any one of its stereoisomers.

11. The method according to claim 3 wherein the compound is 3-butyl-6-methylheptan-2-ol in the form of any one of its stereoisomers.

12. The method according to claim 4 wherein the compound is 6-methyl-3-propylheptan-2-ol in the form of any one of its stereoisomers.

13. The method according to claim 4 wherein the compound is 3-butyl-6-methylheptan-2-ol in the form of any one of its stereoisomers.

14. The method according to claim 5 wherein the compound is 6-methyl-3-propylheptan-2-ol in the form of any one of its stereoisomers.

15. The method according to claim 5 wherein the compound is 3-butyl-6-methylheptan-2-ol in the form of any one of its stereoisomers.

* * * * *

UNITED STATES PATENT AND TRADEMARK OFFICE
CERTIFICATE OF CORRECTION

PATENT NO.         : 8,809,256 B2                                       Page 1 of 1
APPLICATION NO.    : 13/635571
DATED              : August 19, 2014
INVENTOR(S)        : Rautenstrauch et al.

It is certified that error appears in the above-identified patent and that said Letters Patent is hereby corrected as shown below:

<u>Title Page:</u>
Item (73) Assignee, change "Firmenish SA" to -- Firmenich SA --.

Signed and Sealed this
Eleventh Day of November, 2014

Michelle K. Lee
*Deputy Director of the United States Patent and Trademark Office*